United States Patent
Patwardhan et al.

(10) Patent No.: US 10,145,840 B2
(45) Date of Patent: Dec. 4, 2018

(54) SYSTEMS AND METHODS FOR BLOOD SAMPLE PRESERVATION AND HEMATOCRIT SEPARATION

(71) Applicant: Polymer Technology Systems, Inc., Indianapolis, IN (US)

(72) Inventors: Aniruddha Patwardhan, Fishers, IN (US); Gary L. Hughes, Anderson, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 97 days.

(21) Appl. No.: 15/253,628

(22) Filed: Aug. 31, 2016

(65) Prior Publication Data

US 2017/0059551 A1  Mar. 2, 2017

Related U.S. Application Data

(60) Provisional application No. 62/212,991, filed on Sep. 1, 2015.

(51) Int. Cl.
*B01D 63/08* (2006.01)
*G01N 1/28* (2006.01)
(Continued)

(52) U.S. Cl.
CPC .......... *G01N 33/491* (2013.01); *B01D 63/08* (2013.01); *B01L 3/5023* (2013.01); *B01L 9/52* (2013.01);
(Continued)

(58) Field of Classification Search
CPC .. G01N 33/491; G01N 1/4005; G01N 1/2813; G01N 2001/4016; G01N 2001/2826; G01N 33/49; G01N 33/4915; G01N 33/492; G01N 1/34; G01N 1/40; G01N 2001/2733; G01N 2001/4005; B01L 3/5023; B01L 9/52; B01L 2300/105; B01L 2300/0681; B01L 2300/161; B01L 2300/0887; B01L 3/502; B01D 63/08; B01D 63/082; B01D 2311/2626; B01D 2311/2688; B01D 2311/2653;
(Continued)

(56) References Cited

U.S. PATENT DOCUMENTS

| 4,477,575 | A | * | 10/1984 | Vogel | B01D 39/2017 210/509 |
| 4,647,430 | A | * | 3/1987 | Zweig | G01N 33/525 422/424 |
| 5,135,716 | A | * | 8/1992 | Thakore | B01D 61/18 422/412 |
| 5,962,215 | A | * | 10/1999 | Douglas | G01N 33/521 422/417 |

(Continued)

FOREIGN PATENT DOCUMENTS

WO   WO 2014/118551 A1   8/2014

OTHER PUBLICATIONS

International Search Report and Written Opinion dated Nov. 11, 2016, issued in co-pending PCT App. No. PCT/US2016/049772 (13 pages).

*Primary Examiner* — Joseph W Drodge
(74) *Attorney, Agent, or Firm* — Woodard, Emhardt, Moriarty, McNett & Henry LLP

(57) ABSTRACT

A system for preserving a blood sample and removing hematocrit includes a casing, the casing having a sample port and a lateral flow strip in the casing, the lateral flow strip receiving a sample through the sample port, and flowing the sample down a length of the lateral flow strip.

11 Claims, 5 Drawing Sheets

(51) Int. Cl.
*G01N 33/49* (2006.01)
*B01L 3/00* (2006.01)
*B01L 9/00* (2006.01)
*G01N 1/40* (2006.01)

(52) U.S. Cl.
CPC ......... *G01N 1/2813* (2013.01); *G01N 1/4005* (2013.01); *B01L 2300/0681* (2013.01); *B01L 2300/0887* (2013.01); *B01L 2300/105* (2013.01); *B01L 2300/161* (2013.01); *G01N 2001/2826* (2013.01); *G01N 2001/4016* (2013.01)

(58) Field of Classification Search
CPC ........ B01D 2311/2657; B01D 2317/02; B01D 2317/025; B01D 2323/02; B01D 2325/06; B01D 2325/36
USPC ..... 210/645, 650, 651, 321.75, 321.84, 490, 210/500.21, 500.27, 500.36, 506–508; 422/401, 408, 412, 421–424, 430, 534, 422/535; 435/7.21, 7.24, 7.25, 287.3, 435/287.7, 287.8; 436/169, 170, 177, 436/178, 180
See application file for complete search history.

(56) References Cited

U.S. PATENT DOCUMENTS

| | | | |
|---|---|---|---|
| 6,231,815 B1* | 5/2001 | Bainczyk | B01L 3/5023 206/204 |
| 7,867,780 B2* | 1/2011 | Jones | B82Y 5/00 436/514 |
| 8,465,696 B2* | 6/2013 | Huffstodt | G01N 21/78 422/68.1 |
| 2003/0175153 A1* | 9/2003 | Anaokar | C12Q 1/60 422/401 |
| 2005/0227370 A1* | 10/2005 | Ramel | C12Q 1/00 436/514 |
| 2006/0160078 A1* | 7/2006 | Cardy | B01L 3/5023 435/6.11 |
| 2007/0134810 A1* | 6/2007 | Yang | G01N 33/54366 436/514 |
| 2008/0003141 A1* | 1/2008 | Iketani | G01N 33/558 422/73 |
| 2008/0081341 A1 | 4/2008 | Maher et al. | |
| 2010/0099112 A1 | 4/2010 | Zhou et al. | |
| 2012/0094276 A1 | 4/2012 | Buchanan | |
| 2012/0282634 A1 | 11/2012 | Hughes et al. | |

* cited by examiner

SYSTEMS AND METHODS FOR BLOOD SAMPLE PRESERVATION AND HEMATOCRIT SEPARATION

CROSS REFERENCE TO RELATED APPLICATIONS

This application claims the benefit of U.S. Provisional Application No. 62/212,991, filed on Sep. 1, 2015, which is incorporated herein by reference in its entirety.

BACKGROUND

Blood testing for analytes, diseases, infections, and other conditions that may be detected via blood analysis is a useful diagnostic tool. In many situations, such blood testing is burdensome on the patient and requires multiple doctors' visits in order to perform such testing and analyze the results. In a typical scheme, a patient may have to schedule an appointment to have blood drawn many weeks before a doctor's visit, therefore requiring multiple trips and appointments. This is because testing results usually take a week or more to return.

BRIEF SUMMARY

In one embodiment, a system for preserving a blood sample and removing hematocrit includes a casing, the casing having a sample port and a lateral flow strip in the casing, the lateral flow strip receiving a sample through the sample port, and flowing the sample down a length of the lateral flow strip. Optionally, the system includes a blood separation layer in the casing on top of the lateral flow test strip, oriented in line with the sample port. Alternatively, the blood separation layer is approximately a length of the sample port and the lateral flow strip is a length of the casing. In one alternative, the blood separation layer includes a uniform screen side; and the lateral flow strip includes a uniform screen side; and the uniform screen side of the blood separation layer is oriented away from the sample port towards the lateral flow strip; and the uniform screen side of the lateral flow strip is oriented towards the blood separation layer. In another alternative, the casing includes a vent, the vent distal from the sample port. Optionally, the sample preservation system includes a nylon layer oriented in the casing under the lateral flow test strip. Alternatively, the sample preservation system includes a cap, the cap sized to fit in the sample port of the casing. In one configuration, the blood separation layer has been impregnated with inert ingredients to make it hydrophilic and allow red blood cell filtration. In another configuration, the inert ingredients are poly vinyl alcohol and a wetting agent. Optionally, the inert ingredients are poly vinyl alcohol and lectins. Alternatively, the system further includes a pouch for receiving the casing and lateral flow strip combination, the pouch including a desiccant. Alternatively, the system further includes a vial for receiving the casing and lateral flow strip combination, the pouch including a desiccant.

In one embodiment, a method of preserving a blood sample includes providing a sample preservation system including: a casing, the casing having a sample port and a lateral flow strip in the casing. The method further includes receiving a blood sample in the sample port and flowing the blood sample across the lateral flow test strip. Optionally, the method further includes providing a blood separation layer located above the lateral flow strip and in line with the sample port; flowing the blood sample vertically through the blood separation layer; separating the red blood cells with the blood separation layer; and flowing the blood sample to the lateral flow strip from the blood separation layer. In one alternative, the blood separation layer is approximately a length of the sample port, and the lateral flow strip is a length of the casing; and the blood separation layer includes a uniform screen side, and the lateral flow strip includes a uniform screen side; and the uniform screen side of the blood separation layer is oriented away from the sample port towards the lateral flow strip; and the uniform screen side of the lateral flow strip is oriented towards the blood separation layer. In another alternative, the sample preservation system includes a nylon layer oriented in the casing under the lateral flow test strip. Optionally, the sample preservation system includes a cap, the cap sized to fit in the sample port of the casing. Optionally, the method further includes inserting the cap into the sample port to push the sample using air pressure through the blood separation membrane and the lateral flow membrane. Alternatively, the method further includes providing a sample preservation enclosure; inserting the sample preservation system into the sample preservation enclosure; and drying the blood sample in the sample preservation enclosure. In one configuration, the sample preservation enclosure is a sealable bag and includes a desiccant. In another configuration, the sample preservation enclosure is a sealable vial and includes a desiccant.

DETAILED DESCRIPTION

Figure 1:
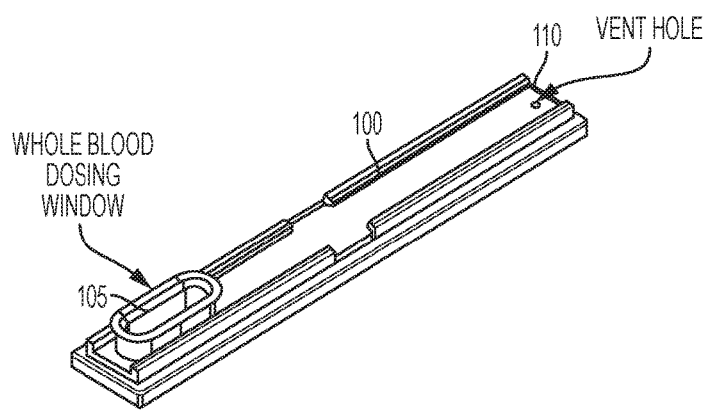
FIG. 1 shows one embodiment of a system for blood sample preservation and hematocrit separation.

Certain terminology is used herein for convenience only and is not to be taken as a limitation on the embodiments of the systems and methods for blood sample preservation and hematocrit separation. In the drawings, the same reference letters are employed for designating the same elements throughout the several figures. Systems and methods for blood sample preservation and hematocrit separation generally include a holder or plastic casing that includes a medium for absorbing a blood sample from an individual. The medium is, in many embodiments, one or more membranes. In many embodiments, a first layer is a blood separation layer. The blood separation layer may separate red blood cells. In many embodiments, a lateral flow test strip is included in the membranes to allow for further blood separation and preservation. In many embodiments, a nylon layer is included to allow for holding and ease of flow.

Generally, embodiments include a blood card/stick that is compact and separates whole blood components like RBC (red blood cells or hematocrit) and WBC (white blood cells) from plasma. The RBC and WBC are concentrated in one portion, while the plasma is wicked onto a membrane for further analysis. Generally, the system is thought to have many advantages including:

1. Low blood volume (80 μL) compared to on-market products (150)μL;
2. Rapid plasma separation (between 2 to 3 minutes);
3. Protects sample from contamination and is tamper resistant;
4. Reduced biohazard exposure;
5. Ambient storage of strip and shipping;
6. Compact design; and
7. Easy to use.

Embodiments provide a method to separate plasma or serum from red blood cells (RBC) and white blood cells (WBC) in whole blood on a solid support. The system uses a single-use strip where the blood is collected and stored as a dried sample. The strip consists of components where the whole blood is separated using a blood separation layer which is in direct fluid contact with a lateral flow membrane. These membranes are kept in a specialized plastic holder with a cap (see FIG. 1.). The cap contains the blood collection receptacle (as shown in FIGS. 1 and 2).

In one embodiment, the architecture and the layers include:
  Layer 1: A blood separation membrane like D-23 which has been impregnated with inert ingredients to make it hydrophilic and allow RBC filtration.
  Layer 2: This layer contains a linear (not spiral, bent or kinked) lateral flow strip.
  Layer 3: A nylon mesh to hold both the membranes and allow for easy plasma flow.

In FIG. 1, one embodiment of a system 100 is shown. The system includes a whole blood dosing window 105 for dosing the correct amount of blood for sample preservation. System 100 further includes a vent 110 that allows for air to escape when a sample is placed in the dosing window 105, such that air pressure does not prevent the expansion of the sample. The system 100 of the blood stick/card measures 2.40 in×0.370 in.

Figure 2:
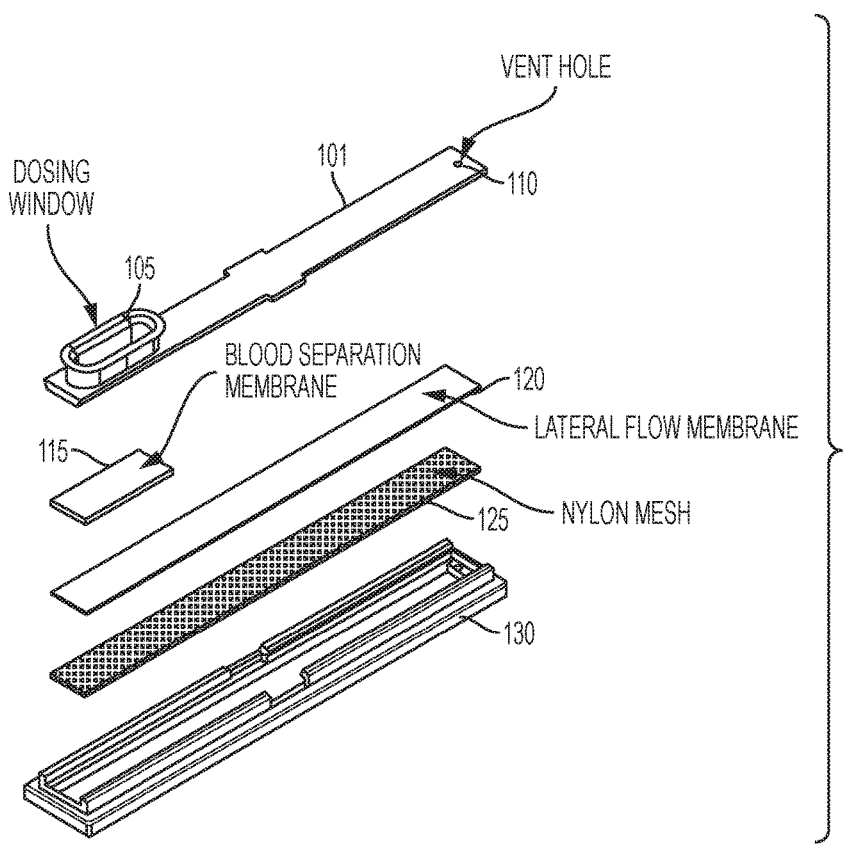
FIG. 2 shows an exploded view of the system of FIG. 1.

FIG. 2 shows an exploded view of the system 100. As shown, a blood separation layer 115 is included under top plastic piece 101. Below that is a lateral flow membrane 120. Beneath that are a nylon mesh 125 and a strip bottom 130.

The plastic holder 101, 130 was designed to minimize contamination and allow easy dosing of the whole blood either by a capillary pipette or by directly depositing the blood by the finger drop. The wide mouth of the application window 105 has been designed to "accommodate" the pear-shared droplet. Moreover, the strip assembly is well contained in the holder to allow for easy operation. The cap, which fits into application window 105, provides necessary compression to affect optimal plasma flow while retaining the RBCs on the blood separation membrane 115. There are no moving parts to the system 100 (as the lid closure shown in PCT Publication No. WO 2015095853A1). The membranes are accessed easily by a simple slight twisting of the body to release the cap without compromising the membrane integrity and structure.

The system 100 includes a blood separation membrane 115 made of a borosilicate glass fiber (D-23) from I. W. Tremont Co., Inc., which provides RBC and WBC filtering capability to concentrate the cells for downstream analysis. The blood separation membrane 115 is rendered hydrophilic with inert ingredients. The blood separation membrane is cut into a 0.50 in×0.20 in (0.10 in$^2$) dimension. The lateral flow membrane, usually an LF1 or MF1 (bound glass fiber filter), provides the necessary capillary action and the solid support medium to wick plasma from the sample. The dimension of the lateral flow membrane (for e.g., LF1) is 0.20 in×2.36 in with an area of 0.472 in$^2$. The length of the lateral flow membrane has been determined using a dosage volume of 80 μL (2 large drops).

Figure 3A:
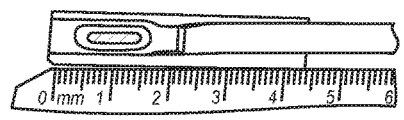
FIGS. 3A-3D show two possible orientations of the layers of the system of FIG. 1 and the resulting impacts on sample flow.
Figure 3C:
Figure 3B:
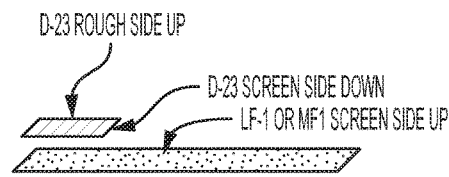
Figure 3D:
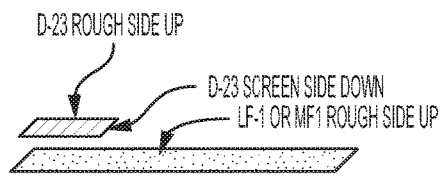
Figure 4:
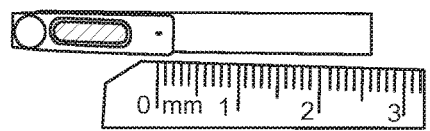
FIGS. 4-6 show the results of including a red blood cell separation layer with the lateral flow strip of the system of FIG. 1.

In some embodiments, the blood separation membrane may have a uniform screen side and a felt side. The felt side typically is more irregular. In some embodiments, the lateral flow membrane may also have a uniform screen and felt side. In some configurations, the uniform screen sides (mesh side) of both layers are positioned such that they face each other (with the uniform side down for the blood separation layer and the uniform side up for the lateral flow layer). During development, it was noted that the sidedness of the LF1 membrane resulted in higher wicking length of the plasma (see FIG. 3). FIG. 3A-D shows an embodiment of an assembly where the D-23 blood separation membrane is stacked with FL1 Membrane and is dosed with 80 μL of whole blood. FIG. 3A shows the RBC's are trapped in the D-23 and the plasma has wicked to up to 30 mm (after 3 min) from the RBC front (beneath the cap). The LF1 membrane is positioned where the screen side is UP (rough side down) is in contact with the blood separation membranes screen side. FIG. 3B shows the preferred architecture where the D-23 screen side is in contact with LF1 or MF1 screen side for efficient plasma wicking (<3 min). FIG. 3C shows the RBC's are trapped in the D-23 ad the plasma has wicked to up to 30 mm (after 5 min) from the RBC front (beneath the cap). The FL1 membrane is positioned where the screen side is DOWN position (rough side up) is in contact with the bold separation membranes screen side. In this position the RBC's are not efficiently separated. FIG. 3D shows the D-23 screen side is in contact with LF1 or MF1 rough side. This membrane orientation causes inefficient blood separations and takes more time for plasma separation (5 min). The bottom side (mesh side) of the membrane, when it was kept in contact with the mesh side of the D-23 membrane, resulted in higher wicking action. This is due to better contact between the two membranes (see FIG. 4). FIG. 4 shows the sample was dosed on the D-23 membrane/LF1 assembly without any compression. The plasma wicked to the end of the strip while keeping the red blood cells contained on the blood separation. The plasma front was 2.5 cm. The mesh side orientation of the LF1 resulted in a plasma wick length of 2.5 cm to 3 cm (25 mm) compared to only 1.6 cm (17 mm) after three minutes of dosing the strip. PCT Publication No. WO20150958531A claims a maximum plasma wick length of 16 mm (1.6 cm).

Figure 5:
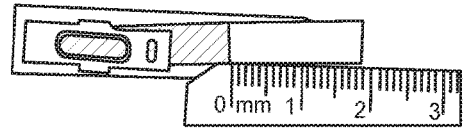
Figure 6:
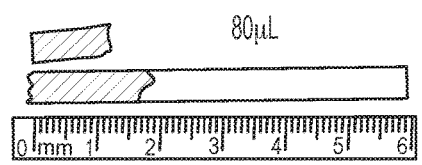

In one strip architecture embodiment, the D-23 membrane and the LF1 membrane were stacked on a mesh. On top of the D-23 membrane, a lid that had an opening for dosing the whole blood was laid. The embodiment shown in FIG. 4 was dosed with 80 μL whole blood. After approximately three minutes, the plasma separated from the RBC and WBC. The plasma wick length was 25 mm. As a "control" strip, the D-23 blood separation membrane 115 was removed and only LF1 membrane 120 was left in the ensemble, which was dosed with 80 μL of whole blood. FIG. 5 shows the extent of the reduced plasma portion where the plasma front length was only 18 mm. This experiment shows that the D-23 blood separation membrane provides for an increase in the plasma wick length and allows for concentration of RBCs on the blood separation membrane. The sample was dosed only on LF1 membrane (no D-23 blood separation membrane) without any compression. The plasma wicked to the end of the strip. Notice that the RBCs wicked to a greater extent. Moreover, the plasma front was only 18 mm in length. In FIG. 6, membranes show the concentration of RBCs on the D-23 blood separation membrane (top membrane) when 80

µL whole blood was dosed. The membranes shows the concentration of RBC's on D-23 Blood Separation membrane (top membrane) when 80 µL whole blood was dosed.

Figure 7:
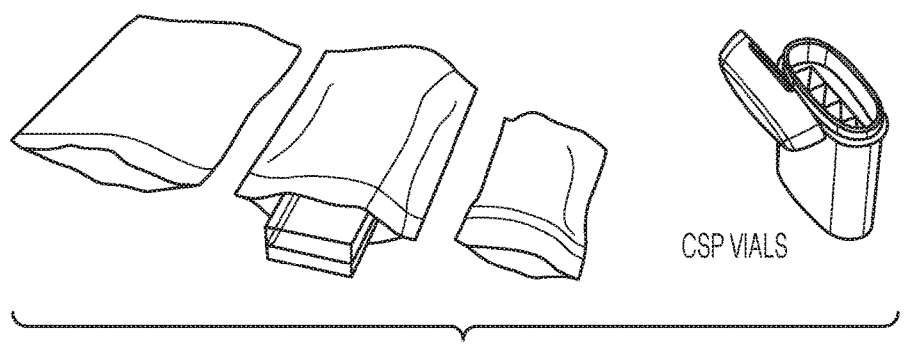
FIG. 7 shows two examples of enclosures for transport and drying of the sample.

Drying, Storage and Shipping:

The strips can be dried using a desiccant-like silica gel or molecular sieves which are contained in the walls of aluminum self-sealing foil bags (see FIG. 7) or vials (for example, CSP vials). This allows the strips to be stored and desiccated at the same time while being shipped to the laboratory for analysis. This convenience is possible because of the strip architecture and the membrane used. The D-23 blood separation membrane allows the blood to be contained in the apparatus and does not allow "back flow" of blood after three minutes of dosing. This feature allows the user the convenience of inserting the strip in the pouch without any biohazard issue.

Analyte Detection from the System for Preserving and Removing Hematocrit (Blood Stick/Card):

The above-mentioned blood stick/card was dosed with 80 µL of blood. The blood stick/card then was dried in a vial (CSP vial) which was enclosed on its wall with molecular sieves. Within 15 minutes, the blood sticks/cards were dried. The blood sticks/cards then were used for detection of two analytes below to demonstrate the concept.

HbA1c Now+:

Three (3) punches measuring 0.125 inches in diameter of the dried D-23 membrane were taken and introduced in the HbA1c Now® sample holder. The sample was shaken thoroughly to ensure complete RBC lysing and then dosed on the HbA1c cartridge using the HbA1c Now+® meter. Table 1 below shows the results are similar to the one obtained from a 5 µL whole blood sample for the same donor.

TABLE 1

| Replicates | HbA1c Values from 5 µL of whole blood in HbA1c Now+ ® POCT meter | HbA1c values from three (3) punches (measuring 0.125 in in diameter each) from D-23 on the HbA1c Now+ ® meter |
| --- | --- | --- |
| 1 | 8.4% | 8.2% |
| 2 | 8.9% | 7.8% |
| 3 | 8.7% | 8.1% |

Cotinine on PTS Detection Device:

The entire length (3 cm) of dried wicked plasma membrane (LF1) was cut in 0.125 inches rectangles and placed in the Cotinine Now® sample holder followed by 100 µL of saline solution (to prevent any absorption of the solution by the membrane). The sample was shaken thoroughly (~two minutes) and then dosed on the Cotinine Now+® meter. Table 2 below shows the results obtained similar to the one obtained from a 40 µL whole blood sample for the same donor.

TABLE 2

| Replicates | Cotinine Values from 40 µL of whole blood in Cotinine Now+ ® POCT meter | Cotinine values from a 3 cm length LF1 membrane on the Cotinine Now+ ® meter |
| --- | --- | --- |
| 1 | 77 ng/dL | 82 ng/dL |
| 2 | 73 ng/dL | 87 ng/dL |
| 3 | 75 ng/dL | 72 ng/dL |

Embodiments of systems for blood sample preservation and hematocrit separation provide a new approach using a blood separation membrane to concentrate the RBCs followed by a wicking layer to separate the plasma for downstream analysis. Importantly, the dried D-23 membrane is able to be used to determine the HbA1c value for the donor. Embodiments also demonstrate that analytes like HbA1c and cotinine can be detected from dried blood separation and the plasma wicking membranes of D-23 and LF1, respectively.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof. Note that, although particular embodiments are shown, features of each attachment may be interchanged between embodiments.

What is claimed as new and desired to be protected by Letters Patent of the United States is:

1. A system for preserving a blood sample and removing hematocrit, comprising:
   a casing, the casing having a sample port; and
   a lateral flow strip in the casing, the lateral flow strip configured for receiving a sample through the sample port and flowing the sample down a length of the lateral flow strip:
   a blood separation layer configured to remove hematocrit In the casing on top of the lateral flow strip, oriented in line with the sample port:
   a sealable sample preservative enclosure: and
   a desiccant received within the sample preservative enclosure,
   the casing and contained lateral flow strip and blood separation layer having a first condition of being separate from the sample preservation enclosure for reception of a sample, the casing and contained lateral flow strip and blood separation layer having a second condition, after having received a sample, of being sealed within the sample preservative enclosure, the desiccant being effective to dry the sample within the sealed sample preservative enclosure, and
   wherein the blood separation layer includes a screen side and an opposed felt side, and the lateral flow strip includes a screen side and an opposed felt side, the screen side of the blood separation and the uniform screen side of the lateral flow strip facing each other.

2. The system of claim 1, wherein the blood separation layer is approximately a length of the sample port and the lateral flow strip is a length of the casing.

3. The system of claim 1, wherein the casing includes a vent, the vent distal from the sample port.

4. The system of claim 3, further comprising a nylon layer oriented in the casing adjacent the felt side of the lateral flow test strip.

5. The system of claim 4, further comprising a cap, the cap sized to fit in the sample port of the casing.

6. The system of claim 5, wherein the blood separation layer has been impregnated with inert ingredients to make it hydrophilic and allow red blood cell filtration.

7. The system of claim 6, wherein the inert ingredients are poly vinyl alcohol and a wetting agent.

8. The system of claim 6, wherein the inert ingredients are poly vinyl alcohol and lectins.

9. The system of claim 5 in which the cap is configured such that insertion of the cap into the sample port pushes the sample using air pressure through the blood separation layer and the lateral flow strip.

10. The system of claim 1, in which the sample preservative enclosure comprises a pouch including the desiccant.

11. The system of claim 1, in which the sample preservative enclosure comprises a vial including the desiccant.

* * * * *